United States Patent [19]
Jackson et al.

[11] Patent Number: 5,485,848
[45] Date of Patent: Jan. 23, 1996

[54] PORTABLE BLOOD PRESSURE MEASURING DEVICE AND METHOD OF MEASURING BLOOD PRESSURE

[76] Inventors: Sandra R. Jackson; Harry E. Jackson, both of 424 W. End Ave., Apt. 11B, New York, N.Y. 10024

[21] Appl. No.: 893,287

[22] Filed: Jun. 4, 1992

Related U.S. Application Data

[63] Continuation-in-part of Ser. No. 648,882, Jan. 31, 1991, abandoned.

[51] Int. Cl.$^6$ .................................................. A61B 5/021
[52] U.S. Cl. .......................................... 128/672; 128/687
[58] Field of Search ................................. 128/672, 679, 128/687, 689, 690, 666.7

[56] References Cited

U.S. PATENT DOCUMENTS

| | | |
|---|---|---|
| 2,756,741 | 7/1956 | Campanella . |
| 3,102,534 | 9/1963 | Bigliano et al. . |
| 3,535,067 | 10/1970 | Lesher et al. . |
| 3,572,316 | 3/1971 | Vogelman et al. . |
| 3,838,684 | 10/1974 | Manuel et al. . |
| 3,880,145 | 4/1975 | Blick . |
| 3,972,320 | 8/1976 | Kalman . |
| 4,030,484 | 6/1977 | Kuska et al. . |
| 4,185,621 | 1/1980 | Morrow . |
| 4,307,727 | 12/1981 | Haynes . |
| 4,331,154 | 5/1982 | Broadwater et al. . |
| 4,423,738 | 1/1984 | Newgard . |
| 4,469,107 | 9/1984 | Asmar et al. ............................. 128/681 |
| 4,703,758 | 11/1987 | Omura . |
| 4,799,491 | 1/1989 | Eckerle . |
| 4,802,488 | 2/1989 | Eckerle . |
| 4,830,017 | 5/1989 | Perry et al. . |
| 4,846,189 | 7/1989 | Sun ..................................... 128/667 X |
| 4,869,262 | 9/1989 | Orr et al. . |
| 4,924,871 | 5/1990 | Honeyager . |
| 4,947,855 | 8/1990 | Yokoe et al. . |
| 4,986,277 | 1/1991 | Sackner . |
| 5,099,853 | 3/1992 | Uemura et al. .......................... 128/679 |
| 5,111,817 | 5/1992 | Clark et al. ............................ 128/666 X |
| 5,140,990 | 8/1992 | Jones et al. ............................. 128/667 |
| 5,165,416 | 11/1992 | Shinoda et al. ........................ 128/672 |

FOREIGN PATENT DOCUMENTS

| | | | |
|---|---|---|---|
| 0297146 | 1/1989 | European Pat. Off. . | |
| 2599616 | 12/1987 | France .................................... | 128/690 |
| 2848198 | 5/1980 | Germany ................................ | 128/690 |
| 3613889 | 10/1987 | Germany ................................ | 128/690 |
| 616801 | 4/1980 | Switzerland .......................... | 128/690 |

OTHER PUBLICATIONS

This Season's Popular Casio Collection Catalog, by Casio, Inc., Dover, New Jersey, pp. 1 and 2.
Hammacher Schlemmer Mid–Winter '92 Catalog, pp. 2 and 15.
Silicon Transducer Strapped to Wrist Reads Blood Pressure, "Electronics", Apr. 28, 1977, pp. 29–30.
A Study of Noninvasive Blood Pressure Measurement Techniques, by C. S. Weaver et al., pp. 89–105.
Technical Note—All–Digital Instantaneous Heart–Rate Meter, by V. C. V. Pratapa Reedy, "Medical and Biological Engineering & Computing", Jul. 1977, pp.472–473.
A Transducer for the Continuous External Measurement of Arterial Blood Pressure, by G. L. Pressman et al., "IEEE Transactions on Bio–Medical Electronics", pp. 73–81.

*Primary Examiner*—Angela D. Sykes
*Attorney, Agent, or Firm*—Stroock & Stroock & Lavan

[57] ABSTRACT

A non-invasive, non-intrusive, convenient and portable device for monitoring a user's arterial blood pressure is provided. The continuous blood pressure monitoring device includes a transducer mounted to detect arterial wall movement caused by blood flow through an artery of the user and means for measuring the output signals of the transducer and accurately converting these signals to systolic and diastolic blood pressure readings on a continuous basis. Calibration data is collected by periodically comparing transducer output signals and the simultaneous outputs of a separate diagnostically accurate blood pressure measuring device (such as a cuff sphygmomanometer), which is not coupled to the device during normal blood pressure monitoring. Blood pressure is computed from the measured transducer output signals and the calibration data.

87 Claims, 7 Drawing Sheets

PORTABLE BLOOD PRESSURE MEASURING DEVICE AND METHOD OF MEASURING BLOOD PRESSURE

This is a continuation-in-part of application Ser. No. 07/648,882, filed on Jan. 31, 1991, now abandoned.

BACKGROUND OF THE INVENTION

This invention is generally directed to a portable blood pressure measuring device providing accurate, essentially continuous readings without requiring affirmative action of the user, and, more particularly, to a device using a transducer and self-contained circuitry to calculate values for systolic and diastolic blood pressure. The continuous measurement of a patient's blood pressure is a virtual necessity to fully comprehend the dynamics of hypertension and other medical problems. Although the medical community does not know all the factors involved in raising and lowering of blood pressure, it is generally agreed that emotional stress, physical exertion and the chemical composition of an individual's blood, such as sodium concentration, affect one's blood pressure.

For those individuals suffering from chronic high blood pressure, there are many medications that can be taken. However, specifying the most appropriate dosages and their optimum timing is currently problematic. In chronic cases of high blood pressure, when a sufferer feels an attack, there are medications that instantaneously reduce the blood pressure of the individual.

However, most individuals are not aware when a gradual, or even sudden, rise in blood pressure has occurred, though such rise in blood pressure can cause heart attacks, aneurysms, strokes and other serious damage. Accordingly, there is a need for a monitoring device that can quickly and continuously monitor a person's blood pressure without inconveniencing or inhibiting the ability to conduct daily life, and without requiring affirmative action of the user during normal use.

Previous monitor systems have relied upon inflation techniques mimicking the original sphygmomanometer based on Riva Rocca's principle in which auscultatory measurements of blood flow are made to determine the systolic and diastolic blood pressure. When the inflation process is automated and mechanized, better control and consistency can be gained, but new possibilities for further error are also introduced. By eliminating the repeated use of the inflation approach, and the inherent problems associated therewith, and using a calibration technique, increased accuracy can be provided.

A non-invasive approach known as the tracking cuff principle relies upon a hydraulic servo control system to maintain a finger arterial volume constant, in which case the counter cuff pressure follows the intra-arterial blood pressure giving an instantaneous blood pressure. This, however, has not proved accurate and because it requires long periods of cuff pressure, it can be painful and uncomfortable to the patient.

Another approach which also has not proved to be accurate and does not provide continuous values of blood pressure is the annular inflatable cuff for placement about a patient's finger. The cuff is inflated to the appropriate pressure and light emitting diodes are provided on the inside of the cuff and a photoelectric transducer is provided on the opposite inner wall of the cuff. The light is partially transmitted through the patient's finger to the photoelectric transducer which measures arterial volumetric changes in the finger. These are transmitted to a microprocessor which controls the inflation and deflation of the cuff around the finger and calculates systolic and diastolic pressure using the Hardy and Collins compliance model in which the pressure-volume relationship of blood vessels is described by an algorithm. This technique has been found intermittent and not dependable when tested (U.S. Pat. No. 4,846,189).

Non-invasive blood pressure monitoring transducers are known in the prior art as exemplified by U.S. Pat. No. 4,423,738 (Newgard). The Newgard patent is directed to a transducer array for arterial tonometry. This invention includes a transducer provided in a case similar to that of a conventional wristwatch. The case is held in place over the radial artery in a human wrist by an expansion band. The transducer is electrically wired to a separate housing that includes the electronic circuitry that converts the electric information to a digital readout. The cord connecting the wrist piece to the housing also includes a source of gas or air to create a constant pressure in the case. The transducer case is required to exert enough pressure against the artery wall to flatten the artery wall. Accordingly, unlike the present invention, this invention requires an external source of gas or air to flatten the user's artery.

A second blood pressure monitoring method and apparatus is disclosed in U.S. Pat. No. 4,802,488 (Eckerle). The Eckerle patent describes a non-invasive method of measuring intra-arterial blood pressure using an array of transducer elements. A set of blood pressure readings is stored in a computer along with pulse amplitude values and information concerning the subject (i.e., age, weight, arm and wrist diameter). From the underlying information, the diameter of the artery can be estimated. Once the diameter of the artery is estimated, the computer knows what portion of the transducer is required to measure arterial pressure and pulse amplitude. The required "hold-down pressure" is supplied by an air pressure source. Accordingly, this invention also suffers from the inability to sample arterial blood pressure without the use of air pressure in a bladder exerting pressure.

Another blood pressure monitoring system is disclosed in European Patent Application No. 0.297,146 which discloses a blood pressure monitoring system which incorporates a conventional cuff and a pulse monitor used in combination to produce a non-continuous blood pressure monitoring system. This system is insufficient in that it requires frequent inflation of the cuff in order to provide a blood pressure reading.

An accurate, non-invasive, continuous method of measuring blood pressure is desirable to allow individuals to monitor their own blood pressure providing for more accurate use of anti-hypertensive medication and preventing overmedication and its side effects. Even in normotensive individuals, there are those with labile hypertension which has gone undetected. Diseases associated with episodes of elevated blood pressure are now being detected with the use of Computerized Axial Tomography ["CAT"] and Magnetic Resonance Imaging ["MRI"] such as multi-infarction dementia in individuals not known to be hypertensive suggesting that monthly visits to a physician's office may not be frequent enough to ensure that an individual is not periodically hypertensive. It is becoming evident that the need for more frequent blood pressure monitoring in the so-called normotensive population is greater than heretofore recognized. Further, having a record of a patient's blood pressure at various points during the day may help in diagnosis and treatment of patients suffering from hypotension as well as from hypertension, and from disorders related to non-normal blood pressure behavior. Hypotension can result in fainting, syncope, or general feelings of weakness or lethargy, and can lead to potentially dangerous losses of functioning. Where patterns of increasing or decreasing blood pressure can be established and treated, they can be controlled before they can cause damage to the individual.

SUMMARY OF THE INVENTION

Generally speaking, in accordance with the instant invention, a non-invasive, non-intrusive, convenient and portable method of continuous blood pressure monitoring is provided. The method includes a first step of mounting a device on the user having a transducer sensitive to the movement of the arterial walls caused by pulsations of one or more arteries in the region where the device is mounted. The second step is setting the nominal pressure of the device (referred to as base pressure) in relation to the user at a desired level. The third step is calibrating the transducer using a sphygmomanometer or other diagnostically accurate blood pressure measuring device which preferably incorporates an electronic output. The sphygmomanometer and transducer are sampled over a period of time and the data received is compared to establish corresponding blood pressure values for the actual transducer readings. The data from the transducer may be checked according to electronically stored algorithms to determine whether a valid reading is received. If a valid reading is received from the transducer, then both the sphygmomanometer and transducer readings may be stored in memory, from which a calibration table for conversion of transducer readings to blood pressure is derived and stored in memory. The calibration table may be adjusted during successive calibrations by the same user based on the cumulative calibration data over a selected number of calibrations.

After calibration, automatic operation of the blood pressure monitor commences. The user's pressure may be read continuously or sampled periodically, and if not within one or more predetermined ranges in a predetermined number of successive samples, an alarm may be activated. Each set of values may be checked and validated to determine whether proper data usable to determine blood pressure has been received. If proper data is received, systolic and diastolic blood pressure values are determined from the instantaneous or averaged high and low pressure values, and the calibration table, and stored in memory. These values may be checked against predetermined levels to set off an alarm. The values may be displayed continuously, periodically or when desired.

Calibration may be performed by an essentially conventional cuff sphygmomanometer which measures blood pressure and wirelessly transmits the blood pressure information to a receiver in the device for use in calibration.

It is an object of this invention to provide a blood pressure monitor that allows for continuous monitoring and storing of blood pressure data throughout the day, without inconvenience to the user.

Another object of this invention is to provide a blood pressure monitor that is small, portable and highly accurate.

Still another object of this invention is to provide a blood pressure monitor that is non-invasive and conveniently calibrated.

Still other objects and advantages of the invention will in part be obvious and will in part be apparent from the specification.

The invention accordingly comprises the several steps and the relation of one or more of such steps with respect to each of the others, and the apparatus embodying features of construction, combinations of elements and arrangements of parts which are adapted to effect such steps, all as exemplified in the following detailed disclosure, with the scope of the invention as indicated in the claims.

BRIEF DESCRIPTION OF THE DRAWINGS

For a fuller understanding of the invention, reference is made to the following description, taken in connection with the accompanying drawings, in which.

DETAILED DESCRIPTION OF THE PREFERRED EMBODIMENTS

This invention is directed to a continuous blood pressure monitor reading systolic and diastolic blood pressure and a continuous pulse rate monitor. The device is configured to preferably be worn around the wrist like a common wristwatch and does not require the use of a cuff or other conventional sphygmomanometer aside from during a calibration process. The CPU within the watch obtains a plurality of data values and incorporates same into a stored database during the calibration process. A transducer is provided on the device, for example, on or within the wristband, for detecting movement caused by the pulsation of arteries in the region where the device is mounted on the user, which is then converted to common blood pressure readings using essentially a table derived during calibration, as opposed to one of the algorithms found wanting in the prior art. In this way, the device is set for the particular physical condition of the user and of the device to provide accurate blood pressure readings. As will be explained below, user conditions are maintained relatively uniform by empirically establishing a standard mounting pressure of the device. Spurious readings due to wrist movement or muscle tightening may be avoided by data screening methods.

After calibration is complete, the calibration is stored within the central processing unit (CPU) or random access memory (RAM) and is accessible by the CPU. Accordingly, for any given transducer output signal, the CPU will generate a systolic and diastolic blood pressure measurement.

This is accomplished by either a direct match with the calibration data received earlier or through electronic data interpretation using determined criteria such as extrapolation, interpolation and the characteristics of the particular transducer used.

The electronic interpretation that takes place, for example, may be by an algorithm such as a linear interpolation from the nearest data points. An analogous approach may be taken for extrapolation beyond the high and low calibration points for systolic calibration readings and diastolic calibration readings. For example, if the calibration reading for the user's systolic blood pressure ranged between 100 and 150 mm Hg, the device may extrapolate systolic pressures below 100 or above 150 mm Hg. The same is true for diastolic values. The interpretation of the transducer signals received is not simply satisfied by an understanding of the conversion curve of the transducer. There may be degrees of variation in spatial displacement (swelling and shrinking) of the body part where the pressure is being measured by the transducer.

The preferred embodiment uses an empirical approach to both interpolation and extrapolation. However, the data for the interpolation is basically the calibration data from the given day or the stored calibration data. Alternatively, the data for the extrapolation would use the present calibration data as well as some other data that, for example, could be preprogrammed into the CPU or RAM prior to purchase or input through an input port. The data accessed could vary depending on personal variables of the user. For example, age, height, weight, physiognomy and gender may be factors in the conversion of transducer signal to blood pressure value. This stored data may be empirically gathered based on data received when control groups representing certain characteristics are tested or based on the testing of the individual involved.

Figure 1:
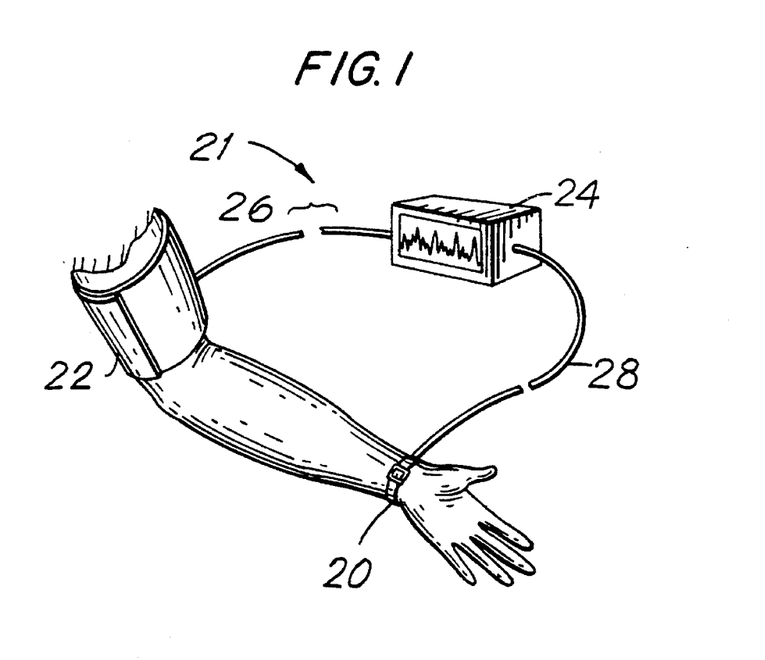
FIG. 1 is a perspective view of a first embodiment of the invention during calibration.

Reference is first made to FIG. 1, wherein a first embodiment of the invention during calibration is depicted. The user is depicted with a wristwatch-type continuous blood pressure monitor, generally indicated at 20, provided on the user's wrist. The blood pressure monitor is shown releasably connected to a conventional, automated cuff sphygmomanometer, generally indicated at 21. Sphygmomanometer 21 includes an inflatable cuff 22, computerized readout 24, and connecting cable 26 and is connected to blood pressure monitor 20 via a connecting cable 28 which is present for calibration purposes. During normal use after calibration, the cuff sphygmomanometer is not required. During installation on the user, the transducer is placed in general proximity to one or more superficial arteries. One embodiment, in the form of a wristwatch-type device with an extended transducer embedded in the strap, facilitates such placement. During calibration, the blood pressure monitor 20 continuously measures blood pressure using a transducer sensitive to movement caused by the pulsations of arteries in the wrist as described below and cuff 22 continuously measures blood pressure via computerized sphygmomanometer 21. The systolic and diastolic blood pressure readings provided by sphygmomanometer 21 and blood pressure monitor 20 are compared to form a calibration table of blood pressure readings stored in monitor 20 as described below.

Figure 2:
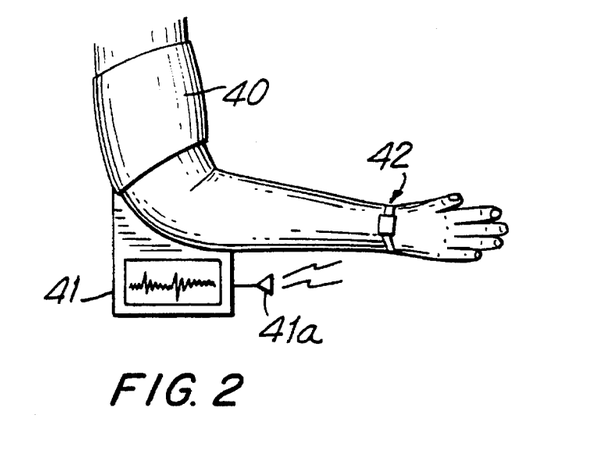
FIG. 2 is a perspective view of a second embodiment of the invention during calibration.

Particular reference is next made to FIG. 2, wherein a second embodiment of the invention depicts a completely automated calibration system, wherein the user uses a conventional automated cuff 40 having transducers therein for reading the arterial blood pressure of the user when the user inserts his arm in the cuff. A plurality of systolic and diastolic blood pressure readings over a desired period of time are wirelessly transmitted by transmitter 41a of sphygmomanometer controller 41 to a wireless receiver component of blood pressure monitor 42. The calibration data from transmitter 41a of sphygmomanometer controller 41 is preferably transferred to monitor 42 as a digital signal. However, this may also be transferred as an analog signal. The wireless receiver is built into monitor 42 and may use an antenna (not shown) built into the band or the housing. A central processor unit (CPU) within blood pressure monitor 42 forms a stored calibration table by comparing the readings received from the sphygmomanometer 41 with the readings from the transducer of blood pressure monitor 42. As described below, blood pressure monitors 20 and 42 both include transducers within the wristband portion, the mounting structure, or the housing thereof to, in one embodiment, detect the arterial expansion and contraction of the arteries within the wrist of the wearer and convert same to blood pressure by a CPU in accordance with the calibration table created during calibration and compensating algorithms as described later.

Figure 3:
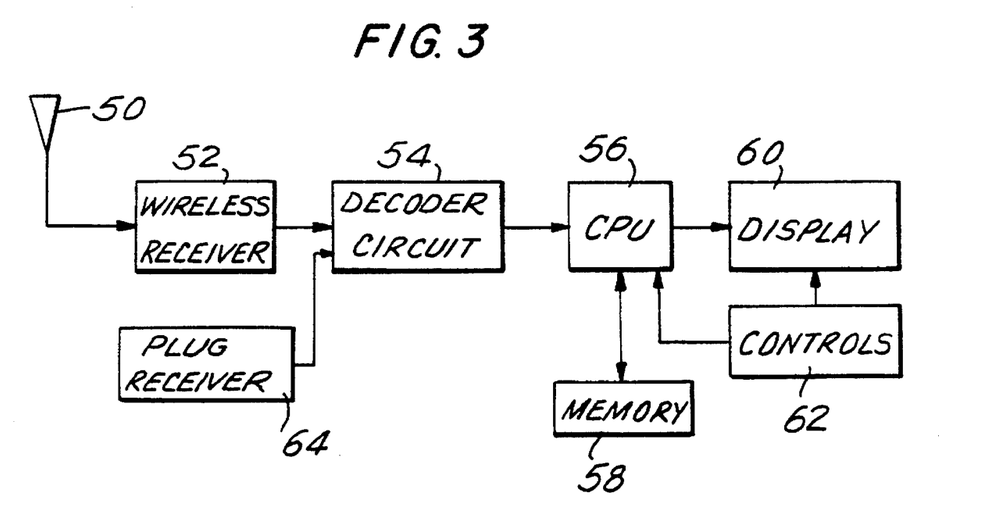
FIG. 3 is a block diagram of the wireless receiver circuit of FIG. 2.

Reference is next made to FIG. 3, wherein a general block diagram of monitor 42 is disclosed. Antenna 50 is adapted to receive an external signal from the wireless transmitter of the sphygmomanometer. The external signal received by antenna 50 is converted into a digital signal by wireless receiver 52. The digital signal is then checked by decoder circuit 54. If decoder circuit 54 determines that the external signal contains valid blood pressure information, then the external signal is transmitted to CPU 56. Memory circuit 58 and display 60 are coupled to CPU 56 and receive the information from CPU 56. A control 62, representative of the buttons, switches, winding stems or other control devices carried by the monitor, permits the user to set monitoring intervals, alarm values and other desired variables, to reset the monitor for different users and to select values for display as desired in a particular embodiment. A plug receiver 64 for releasable connection to a sphygmomanometer as shown in FIG. 1 may be provided in addition to or in place of antennas 50 and wireless receiver 52 to receive sphygmomanometer readings from a releasably plugged in sphygmomanometer and converting same to digital form.

Figure 4:
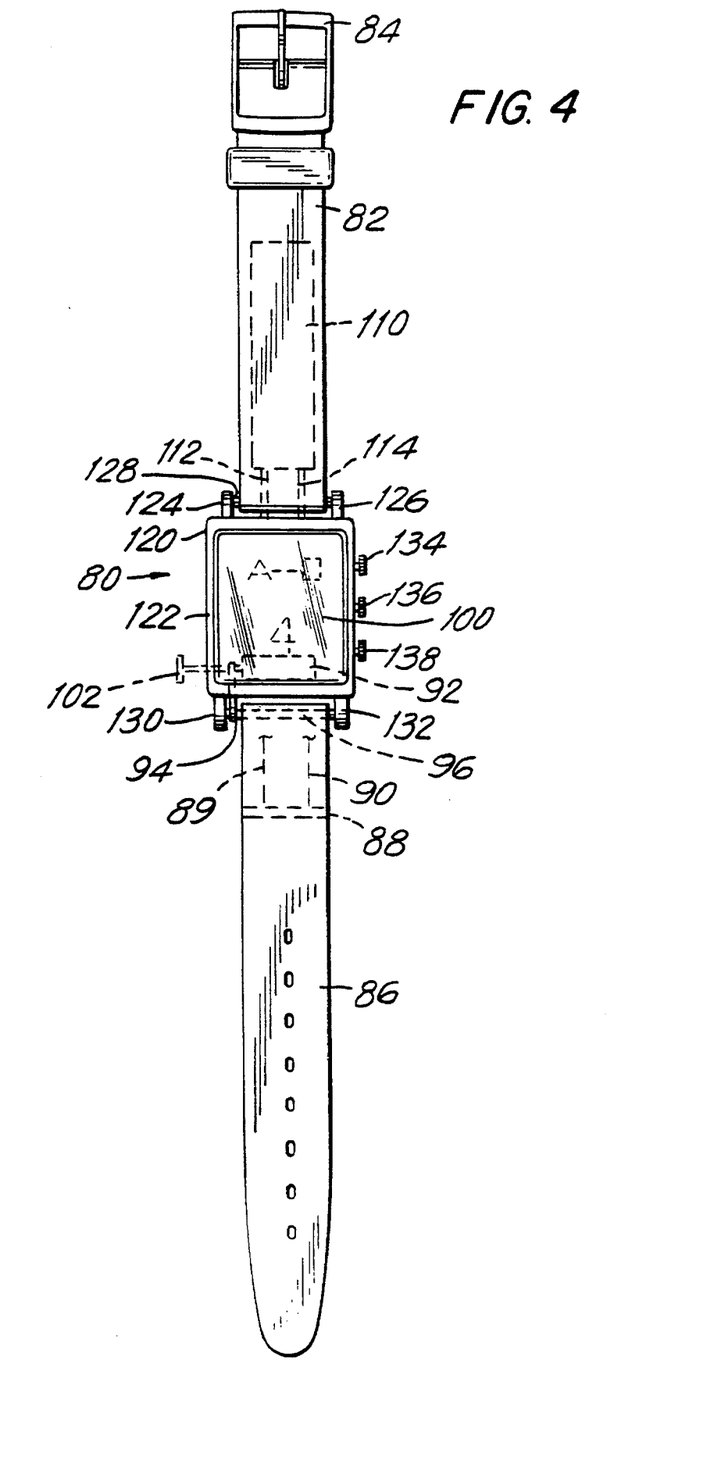
FIG. 4 is a top plan view of a first embodiment of the blood pressure monitor, in accordance with the invention.
Figure 5:
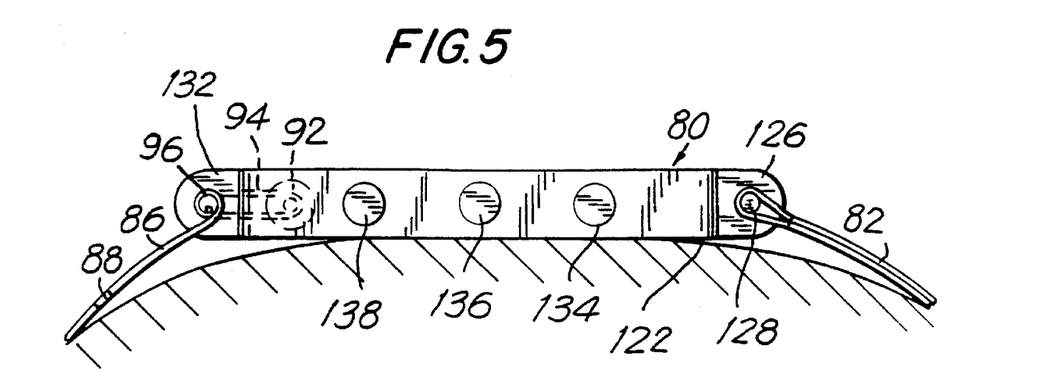
FIG. 5 is a fragmentary enlarged right side elevational view of the embodiment of FIG. 4 mounted on the wrist of a user.

Reference is now made to FIGS. 4 and 5, wherein a blood pressure monitor, generally indicated at 80, is depicted. Blood pressure monitor 80 includes a first band portion 82 and a buckle 84. Second band portion 86 includes a plurality of apertures therein for securing band portion 82 with second band portion 86. Second band portion 86 includes a sensor 88 formed therein for determining the tension on the band. Leads 89 and 90 are coupled to the central processing unit (not shown). The tension on the band should be maintained substantially constant at a predetermined level so that the blood pressure monitor maintains its calibration.

Motor 92 is depicted in phantom and is operated by the CPU to maintain the band at a substantially constant tension. The substantially constant tension may be substantially the same as the calibration tension. However, by incorporating electronic compensation, they need not necessarily be the same. The motor is coupled by a belt 94 to a shaft 96 to which is connected the end of second band portion 86. Shaft 96 is rotated by belt 94 and motor 92 and second band portion 86 is expanded or contracted accordingly, to fully control the standard base pressure to a predetermined level. Coarse pressure adjustment is by the selection of the aperture in which the buckle 84 is engaged. The actual base pressure may be displayed on display 100.

In an alternative embodiment, wherein motor 92 is not used, the display portion 100 of the watch would display the actual base pressure (tension) on the wristband and the calibration base pressure and, accordingly, the band could be adjusted using manual control 102 shown in phantom. This would require only a simple twist to loosen or tighten the band for fine pressure adjustment. The desired base pressure, or range of acceptable base pressures, may be set by manipulation of controls such as buttons 134, 136 and 138, which can also control whether base pressure is to be displayed. As described above, a change of base pressure from the desired level during use may be indicated by an audible or visual alarm in monitor 80.

Alternative means for measuring the base pressure on the band without providing a separate sensor, for example sensor 88, may be used. For example, transducer 110 may additionally serve this purpose. Further, as described below, there are also other means for maintaining the desired base pressure.

By way of example, transducer 110 is used to sense the changes in pressure caused by the periodic expansion and contraction of the arteries in the wrist caused by the periodic contractions and relaxations of the heart. This transducer is positioned such that at least a portion of it contacts the user's skin in the vicinity of one or more superficial arteries. Other transducers responsive to the variations in blood flow through the arteries of the wrist may be used. Transducer 110 converts the variations in blood pressure (manifested by the expansion and contraction of one or more arterial walls) to electrical signals. These electrical signals are transmitted to the central processing unit by leads 112 and 114. The watch/watchband structure is required to be held in contact with the wrist area under a suitable, stabilized level of pressure. In the embodiment depicted, the transducer is provided within the watchband to better detect changes in pressure, but, depending on the type of transducer, could also be mounted on the bottom of case 122. The transducer can take many forms. For example, the transducer can employ a direct physical effect, such as a piezoelectric effect. Alternatively, the transducer could rely on indirect conversions through a form of aneroid chamber, strain gauge, optical motion sensing or hydraulic sensing, or some combination of these effects. The operation of transducer 110 and its interrelationship with the CPU is more explicitly stated with regard to the block diagram of FIG. 9 and the flow chart of FIGS. 10A and 10B.

As stated above, a piezoelectric film may be used as the transducer. A discussion of the operation of an exemplary piezo film follows:

Area=$A=1$ cm$^2$,

Permittivity=$E=106 \times 10^{-12}$ F/m

Thickness=$t=28 \times 10^{-6}$ m

Piezo strain Constant=$d'=-22 \times 10^{-12}$ (c/m$^2$)/(N/m$^2$)

Stress=$x=-10^6$ N/m$^2$

Charge generated:
$Q_1=d_1XA=(-22 \times 10^{-12}$c/m$^2$/N/m$^2$) $(-10^6$N/m$^2$) $(1 \times 10^{-4}$ m$^2$)
$Q_1=2.2 \times 10^{-9}$ Coul Film capacitance=$C_1=E$ A/t $$C_1 = \frac{(106 \times 10^{-12} \text{ F/m}) (10^{-4} \text{ m}^2)}{28 \times 10^{-6} \text{ m}} = 379 \times 10^{-12} \text{ Farads}$$

The above charge $Q_1$ on the electrodes having a capacitance $C_1$ results in a voltage difference between the electrodes as follows:

$V_1=Q_1/C_1=(2.2 \times 10^{-9}$ Coul/$3.79 \times 10^{-10}$ Farads)=5.8 volts.

Accordingly, in the exemplary embodiment shown hereinabove, the stress of $-10^6$ N/m$^2$ produces a voltage of 5.8 volts. The formulas used in calculating $V_1$ clearly show that the voltage produced at the electrodes for this embodiment is proportional to the stress applied to the piezo film. However, such a proportional relationship between the stress applied to the sensor and the signal produced by the sensor is not a critical element of the invention since well-known electronic techniques can be applied to correct for more complex transducer characteristics.

The body 120 of the continuous blood pressure monitor 80 includes a display 100. Display 100 is enclosed on six sides by case 122 which is transparent on the side in closest proximity to the display. Case 122 has posts 124 and 126 for receiving a shaft 128 therethrough. Shaft 128 is used to affix first band portion 82 to case portion 122. Posts 130 and 132 are provided to hold shaft 96, the operation of which is described hereinabove. Display 100 may be an analog display driven by a digital to analog converter in response to the digital signal from the CPU to the analog display. However, in the more preferred embodiment, the display is either a light-emitting diode display or a liquid crystal display, preferably the latter because of low power consumption. The device is preferably powered by a battery shown schematically as 140. With present advancements of liquid crystal display technology, it may be most preferred to use a liquid crystal display and, accordingly, the display can display numerous data, for example, pulse rate, systolic blood pressure and diastolic blood pressure. Further, using a programming function, a variety of stored data, such as the highest blood pressure in a predetermined period of time, such as 24 hours, may be displayed, as well as the threshold blood pressures which will cause an alarm to sound or be visible. A dynamic graph, representative of the contraction and relaxation cycle of the heart as manifested by the expansion and contraction of the arterial walls, can also be presented on the display, either continuously or at the selection of the user or a physician. Other information, such as time, day and date information, may also be displayed. Display 100 may also display alarm conditions or a symbol indicating when calibration is complete. Using conventional liquid crystal technology and watch display techniques, one or more values of time or blood pressure function may be selectively displayed and/or set using buttons 134, 136 and 138, or said other buttons and selection and setting members as may be required depending on the number of functions to be displayed. Periodic blood pressure readings over a predetermined period and at predetermined intervals may be stored and selectively displayed by manipulation of buttons 134, 136 and 138.

As noted, also provided on the housing 122 are three control buttons 134, 136 and 138 for interfacing with and controlling the CPU and display. These buttons, for example, are the function, programming and light display controls. These buttons could be used to program the alarm, to change the display of information on the display 100 and for otherwise programming the information incorporated thereon using conventional techniques.

Figure 6:
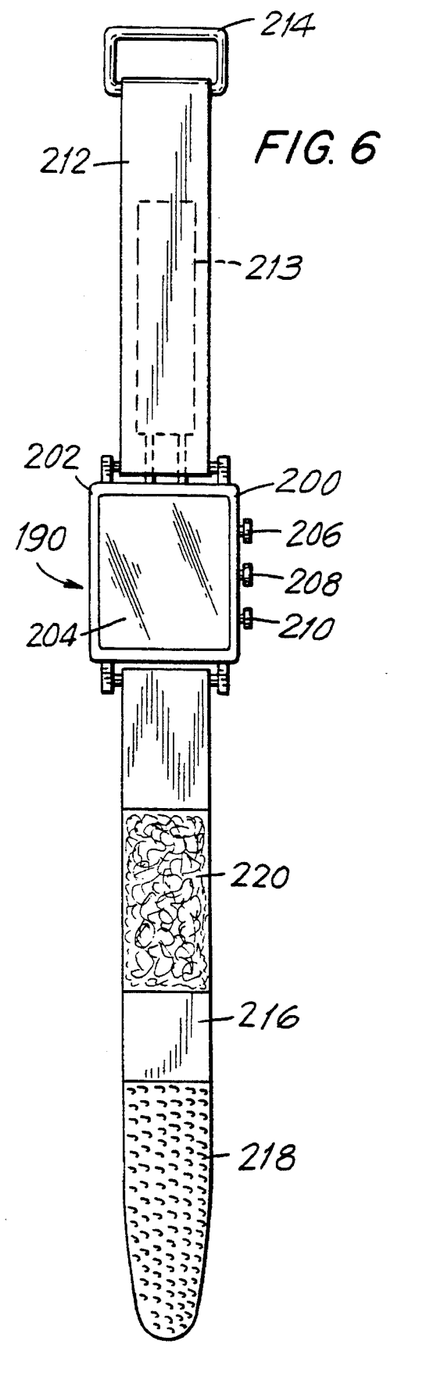
FIG. 6 is a top plan of a second embodiment of the blood pressure monitor.

Reference is next made to FIG. 6, wherein a second embodiment of this invention is depicted. FIG. 6 depicts a monitor 190, which includes a body portion 200 similar to that of body portion 120 of FIGS. 4 and 5. The body portion includes housing 202 with a display 204 incorporated therein. Controls 206, 208 and 210 function as described hereinabove with regard to like elements in FIGS. 4 and 5.

First band portion 212 is formed of nylon or the like and supports at its end a rectangular bail 214 for receiving second band portion 216 therethrough. Second band portion 216 supports the two elements of a hook and loop fastener, namely, array of hooks 218 and array of loops 220. Accordingly, when second band portion 216 is inserted through bail 214 of first band portion 212, and is folded over so that at least a portion of hooks 218 engage at least a portion of loops 220, a continuously adjustable coupling of the monitor 190 on the wrist of the user may be achieved. The hook and loop fastener provides the user with the ability to adjust the base pressure exerted by the band upon the user's wrist to the desired level as measured by transducer 213 and as displayed on display 204. Further, if the user's wrist swells or contracts during the day or night, resulting in a change in base pressure beyond the desired range, the hook and loop fastener may be loosened or tightened by very small amounts to maintain the appropriate pressure on the wrist without the use of a motor or other automatic means of adjustment.

As noted above, transducer 212 located on first band portion 213 is capable of sensing the varying blood pressure of the user and is also capable of sensing the base pressure exerted by the band upon the user's wrist. Thus, in this embodiment, when the base pressure is outside the predetermined range, an alarm sounds and the base pressure can be seen on the display. The user can then manually adjust the base pressure to the appropriate pressure.

Figure 7:
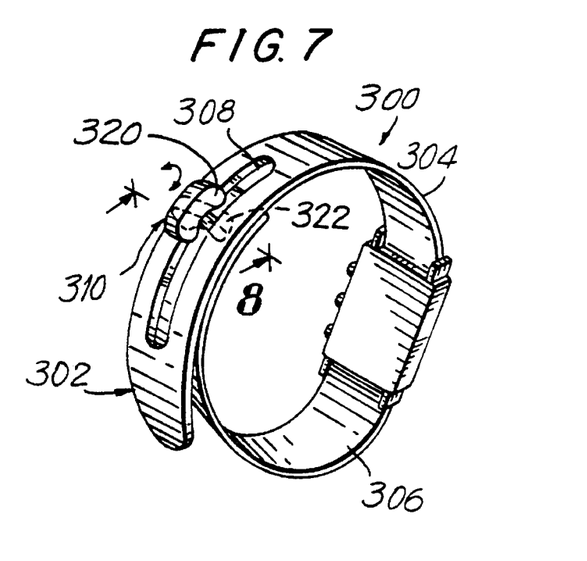
FIG. 7 is a top plan of a third alternative embodiment of the blood pressure monitor.
Figure 8:
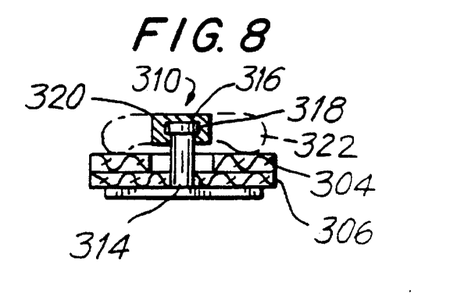
FIG. 8 is a cross-sectional view taken along line 8—8 of FIG. 7.

FIGS. 7 and 8 disclose another alternative embodiment for maintaining the predetermined pressure by the watchband upon the user's wrist. Reference is particularly made to FIGS. 7 and 8, wherein a third embodiment of a blood pressure monitor, generally indicated at 300, is depicted. The operation of the blood pressure monitor, display element and control knobs is similar to that of FIG. 4. This embodiment specifically discloses an alternative method of adjusting base pressure such that the base pressure can be manually adjusted to a desired pressure without use of a motor or reel arrangement of FIGS. 4 and 5.

Watchband 302 includes a first portion 304 and a second portion 306. First portion 304 of watchband 302 is formed with a longitudinal slot 308 therein for receiving a locking member 310 of second band portion 306. Second band portion 306 includes a transducer 312 formed on its inner surface. Locking member 310 includes a shaft 314 coupled to second band portion 306 by a rivet, adhesive or the like. Shaft 314 is formed with an enlarged head 316 having a continuous flange 318 formed therearound. Flange 318 supports wing member 320 so as to be freely rotatable about the axis defined by shaft 314.

In FIG. 7, wing member 320 is depicted in parallel to slot 308 and, accordingly, the second band and first band can move relative to each other to permit removal or mounting of the monitor 300. Wing member 320 can be rotated to position 322 shown in phantom in FIG. 8, at which it locks first band portion 304 and second band portion 306 in place with relation to each other, because the space between the wings of wing member 320 and second portion 306 is slightly less than the normal thickness of first band member 302, requiring compression of the first band member to rotate wing member 320 to position 322. Thus, it can be seen that this locking feature permits continuous and small adjustments of base pressure to be made easily by the user.

A waveform of the displacement of the wall of an artery due to blood pumping by the heart has a periodic shape. The peaks of the wave represent maximum pressure and correspond to the systolic blood pressure and the troughs of the waves represent minimum pressure and correspond to the diastolic blood pressure. The CPU can distinguish between legitimate blood pressure information and displacement of the transducer due to wrist movement or muscle flexing due to the lack of periodic nature of the latter. However, if a full record of all pressure changes is required, it could be recorded by the monitor, although in the normal operation, spurious, nonperiodic measurements are filtered out and discarded by the monitor in developing blood pressure data.

During each calibration, a series of diastolic pressure and systolic pressure readings from the sphygmomanometer and the transducer are stored to form the calibration table. After each successive calibration, performed once or twice a day, a predetermined number of values are stored in the calibration table, so that the blood pressure monitor can actually become more accurate as it stores more data. Once a desired number of readings at various levels are stored, new values can replace or refine old values in the table if at similar locations on the scale.

Figure 9:
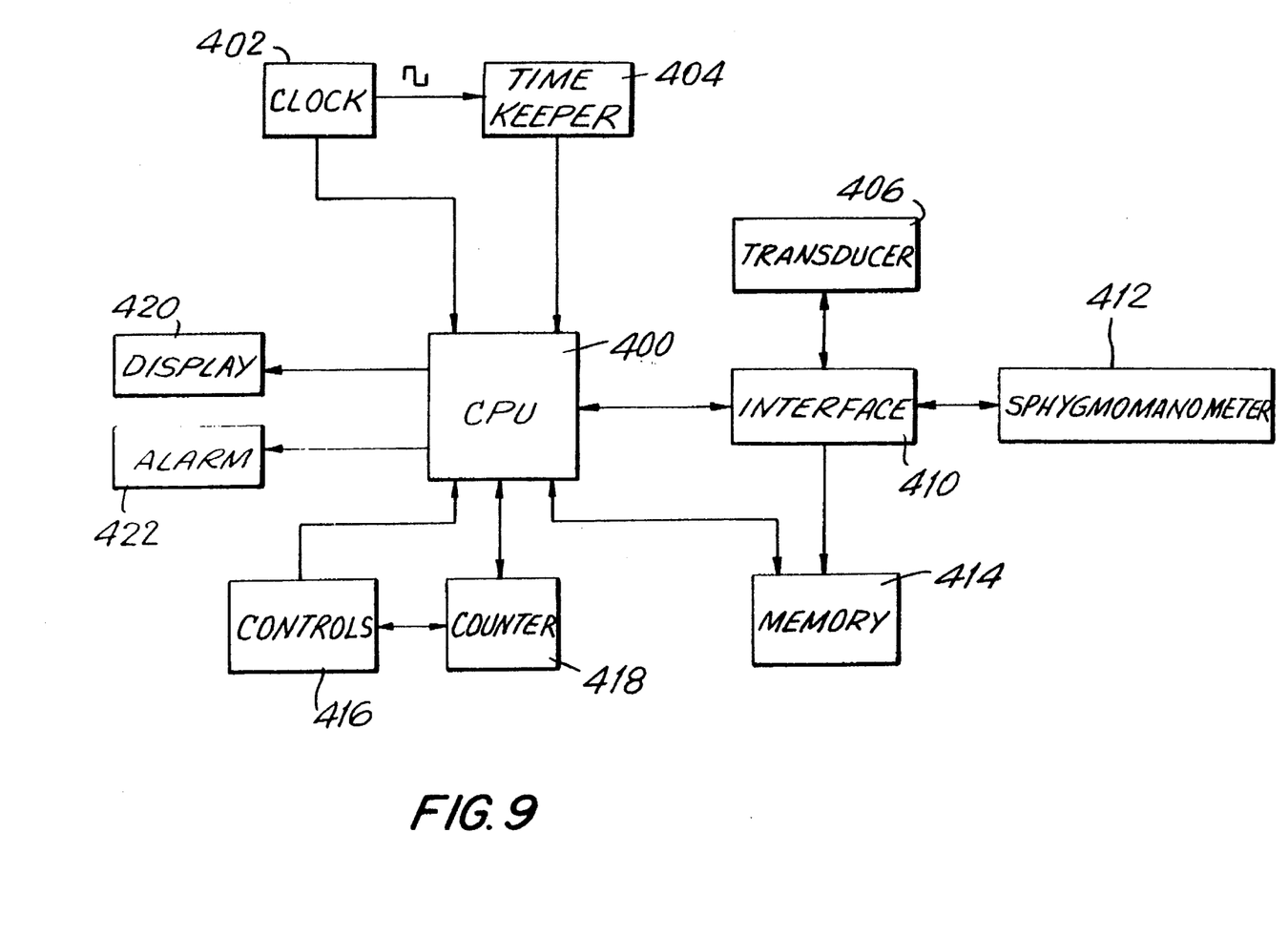
FIG. 9 is a block diagram in accordance with the present invention.

Reference is now made to FIG. 9, wherein a block diagram of the circuit of the monitor in accordance with the invention is depicted. CPU 400 is the center of the operation of the circuit. A clock pulse generator 402 is provided for timing in the circuit. Clock pulse generator 402 feeds the clock pulse to a timekeeper circuit 404 which maintains the time, day and date and provides same to the CPU 400 for application to the display 420. Clock pulse generator 402 also transmits the clock pulse to CPU 400 to provide timing for the circuit.

Calibration is performed as described hereinabove by providing data from a sphygmomanometer 412 and from the transducer 406 to an interface 410 for application to the CPU 400 for the creation of a calibration table of the transducer readings and sphygmomanometer readings in the memory 414 which may or may not be located within CPU 400. The sphygmomanometer and transducer each input data in controlled synchronization to the interface. The CPU controls the interface which determines if the transducer data is valid and usable (having appropriate periodicity and with other parameters within known correct ranges of validity) and determines the systolic and diastolic pressure values measured by the transducer and expressed in electrical units. The approved, processed, and coordinated values are applied to the memory in the addresses assigned for the calibration table. Systolic and diastolic values can be determined from the transducer values as averages of several peaks and troughs to improve accuracy.

Further, the CPU may access stored calibration data in memory 414 to use to translate measured transducer values to pressure values for storing in memory and for displaying. The stored pressure data may be accessed by the user or the user's physician by manipulation of the controls (e.g. buttons) 416 to determine how the user's blood pressure varied throughout the day, week or month, the frequency of storage being also settable. Further, the housing 122 of FIGS. 4 and 5 may be provided with an interface so that the information stored in memory may be downloaded to another computer or to a printer.

As noted, the continuous blood pressure monitor is designed to learn from each calibration. Accordingly, the stored calibration data will continuously be banked in memory and the more calibrations the device goes through, the more accurate the device will become. In an alternative embodiment which would be less expensive to manufacture, the device could have its memory cleared each time a new calibration is conducted. However, it is preferable to store all the calibration data from a number of calibrations to give the CPU the largest amount of data from which to accurately calculate further blood pressure readings. Where there is no calibration data for a transducer value, the CPU will perform a type of extrapolation or interpolation based upon the calibration data and the characteristics of the transducer to obtain a blood pressure reading.

Controls 416 are connected to CPU 400 and to counter 418 which is also connected to CPU 400. In certain modes, a control (button) may be depressed a selected number of times and each time the control is depressed, the counter counts up 1 and sends a new count to the CPU. In response to the count, the CPU may send a different signal to display 420 or perform a different function. In an exemplary embodiment, the counter may count up to 4 then return to 0. In this way, four different displays or functions would be possible from one control. Alarm 422 which is also connected to CPU 400 may be an audible (buzzer) or visual (lit region or message in display 42) and a control may be adapted to shut it off.

As discussed hereinabove, one such piece of information that may be displayed is the pulse rate of the user. This information can easily be calculated by calculating the periodicity of the signal received by the transducer and calculating the number of peaks per 60 second interval. This will give a recognizable pulse rate.

Figure 10A:
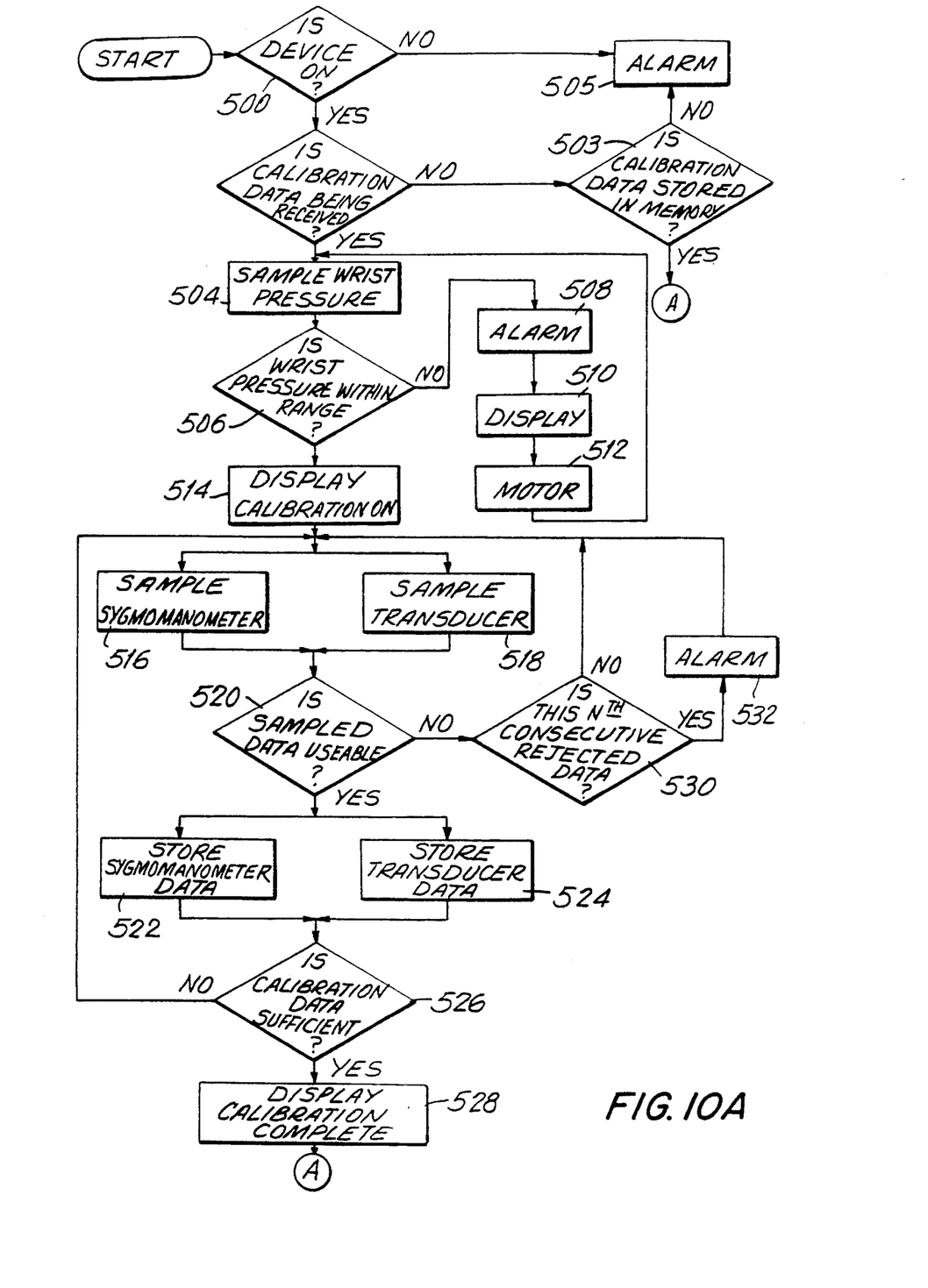
FIGS. 10A and 10B are flow charts of the operation of an embodiment of the invention.
Figure 10B:
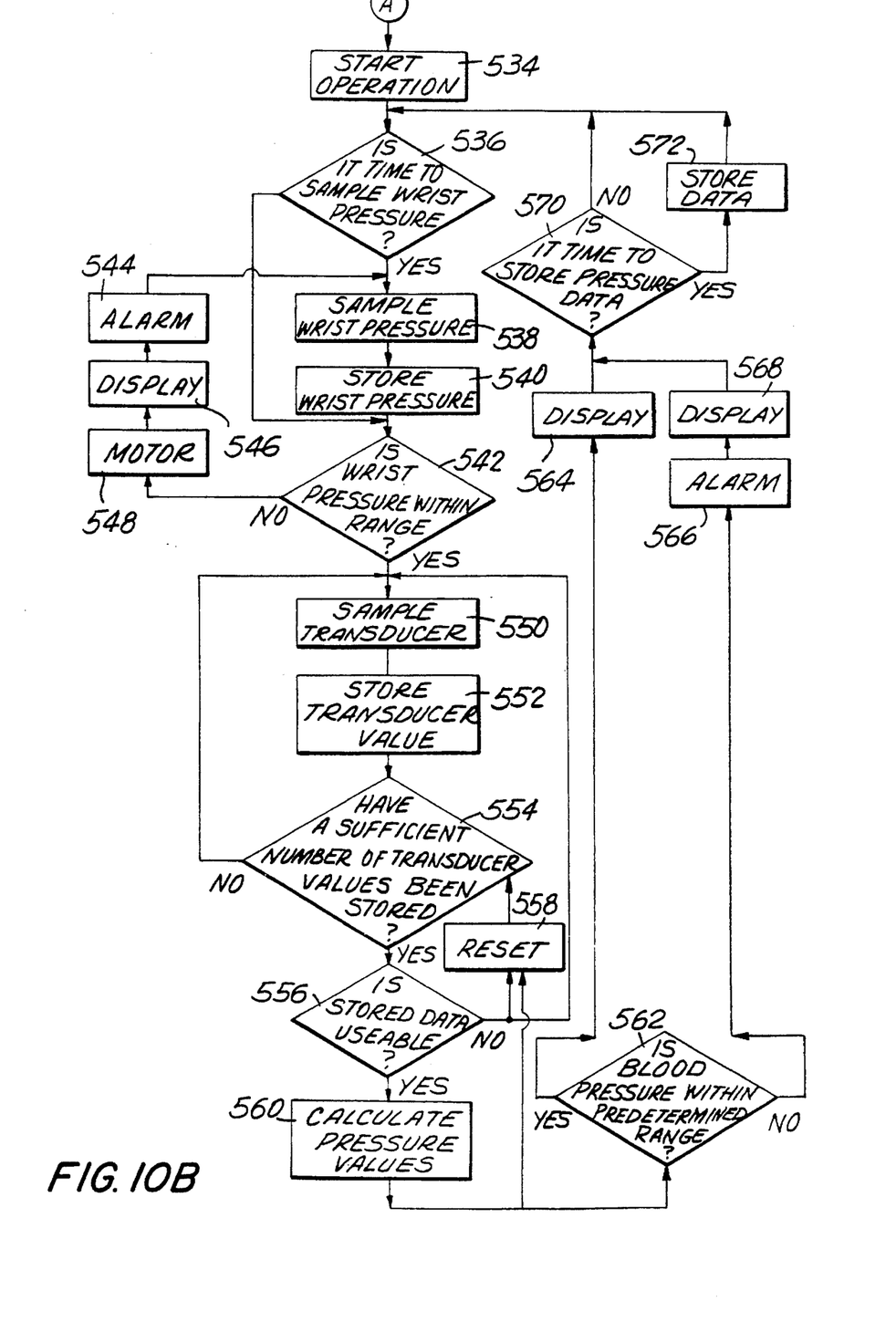

Reference is next made to FIGS. 10A and 10B, wherein a flow chart of the actual operation of one of the preferred embodiments is depicted. This is not the only possible flow chart of operation but is an exemplary embodiment and is not intended to limit the invention to only this method.

FIG. 10A depicts a flow chart of operations involved with calibration of the blood pressure monitor. This flow chart assumes there are two sensors, one being the transducer that senses the arterial expansion, and a second transducer that senses only the stress on the wrist by the band (base pressure). (However, as described hereinabove with regard to FIGS. 6–8, one transducer may sense both base pressure and arterial expansion and contraction.)

In the embodiment of the flow chart of FIG. 10A, the process starts at logic block 500 which determines if the device is on. If NO, the cycle is not continued. If YES, logic block 502 determines if calibration data is being received. This may be either by sensing an output at a receiver or at an interface input. If logic block 502 provides a NO indication, then logic block 503 determines if calibration data is in memory. If logic block 503 determines that NO or insufficient calibration data is in memory, then alarm 505 is activated to tell the user that the device requires calibration. If logic block 503 provides a YES indication, then the process proceeds to point A at which the loop exits to the pressure reading process as shown in FIG. 10B. If logic block 502 provides a YES indicating that calibration data is being received, a sample base pressure operation 504 is performed. Logic block 506 determines whether the base pressure is within range. If the result is NO, one or more of alarm 508, display 510 or motor 512 are actuated. Motor 512 will provide for automatic adjustment of base pressure while display 510 and alarm 508 would alert the user to make manual adjustment. Further, the process returns to the sample base pressure 504 step in this case.

If base pressure is within the predetermined range, the process continues to display "CAL ON" 514, to provide the user with an indication that calibration is continuing. The latter display is optional. A sample sphygmomanometer 516 and sample transducer 518 process is then actuated. The sample transducer process samples the transducer at a relatively high rate, stores the data and examines the data to determine if it is usable data, a step represented by logic block 520. The data received from the external diagnostically accurate sphygmomanometer, such as the cuff sphygmomanometers depicted in FIGS. 1 and 2, is likewise examined for its usability in logic block 520. If the corresponding data is not usable as indicated by a NO in logic block 520, logic block 530 determines if this is the Nth consecutive rejected data, N being a predetermined number. If the output of logic block 530 is NO, the process returns to the sample steps 516 and 518. If a predetermined number of consecutive rejected data is received, as indicated by a YES at logic block 530, alarm 532 is actuated to alert the user to the problem and, if desired, the sample process can continue. If the sample data is usable as indicated by a YES in logic block 520, then a stored sphygmomanometer 522 and stored transducer 524 values steps are taken. Logic block 526 determines if sufficient calibration data is stored. If not, the sample process continues. If YES, then an optional display "CAL COMPLETE" 528 is performed to tell the user that calibration is complete and the user can remove his arm from the cuff sphygmomanometer. At this stage, the calibration table in memory is complete with sufficient data to enable operation and the process continues to point A, at which point the process continues in the flow chart of FIG. 10B.

Referring to the flow chart of FIG. 10B, from point A, a start operation function 534 is activated. Logic block 536 determines if it is time to sample base pressure. This sampling can be done in a predetermined interval which can be set by the control. If logic block 536 indicates a YES, the sample base pressure operation 538 is performed and the sample base pressure is stored as represented by block 540. Logic block 542 then determines if the base pressure is within the predetermined range. If the answer is NO, then alarm 544, display 546 and motor 548 functions are actuated, in a manner similar to like functions 508, 510 and 512 discussed above. Further, the process returns to the sample base pressure function 538 in the cycle since blood pressure measurement is inappropriate until base pressure is within the predetermined range, in order to ensure that the conversion from transducer value to blood pressure is accurately performed. If the output of logic block 536, which determined whether it was time to sample base pressure was NO, the process would revert to logic block 542 to determine if base pressure was within the range. The NO consequence in that logic block is discussed above. A YES consequence would result in a sample transducer operation 550, followed by a store transducer value function 552. As noted above, a plurality of transducer values must be sampled and stored in order to have sufficient data to determine if the data is usable, in other words, to determine if the data represents blood pressure values or other spurious signals such as wrist movement or muscle movement. Logic block 554 determines whether a sufficient number of transducer values have been stored. If the result is NO, the process returns to the sample transducer 550 step. If the answer is YES, then the CPU determines if the stored data is usable as represented by logic block 556. If the stored data is not usable, a reset function 558 resets the count in logic block 554 to zero and returns to the sample transducer 550 step. If the stored data is usable, then the CPU performs the calculate pressure values step 560, first determining the average peak and trough values in terms of measured voltage from the transducer, and then translating that to pressure values using the calibration table. After the desired pressure values have been calculated, the reset function 558 is again performed to reset counter logic block 554 to zero. Logic block 562 then determines if the calculated pressure values are within one or more predetermined ranges. If the answer is NO, alarm 566 and display 568 functions are performed. If the answer is YES, display function 564 is performed. In either event, after the display function 568 or 564 is performed, the cycle continues to logic block 570 which determines if it is time to store pressure data. This function can be manually reset to permit storage of pressure data at any desired interval. If the response to logic block 570 is YES, store function 572 is performed. If the answer is NO or after the store function 572 is performed, the cycle returns to logic block 536, to determine if it is time to sample base pressure.

By the foregoing process, first base pressure is set, then calibration data is gathered, and then continuous blood pressure readings are performed. As noted, the foregoing flow chart is meant by example, not by way of limitation. Various alarm and display functions need not all be provided, and additional alarm and display functions can be provided. The frequency and time at which the base pressure measurement is performed can, for example, differ from the foregoing block diagram, as desired in a particular application. In order to save battery power, the device can optionally function on a periodic rather than on a continuous basis, but continuous operation is a preferred form in view of its medical implications.

It will thus be seen that the objects set forth above, among those made apparent from the preceding description, were efficiently attained and, since certain changes may be made in carrying out the above method and in the construction set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A method of blood pressure monitoring, comprising the steps of:

mounting a transducer on a user's body so that it detects at least one of spatial displacement and pressure variations caused by blood flow through an artery;

mounting a blood pressure measuring device which provides accurate and diagnostically meaningful blood pressure results on a user's body;

collecting calibration data for the transducer while so mounted by comparing a transducer output signal with an output from said blood pressure measuring device;

determining a base pressure applied to the transducer by the step of mounting the transducer to maintain substantially constant pressure on the transducer within a predetermined range of values;

disconnecting said blood pressure measuring device from the user's body;

after disconnecting said blood pressure measuring device, measuring the output signals of the mounted transducer; and computing blood pressure from at least said measured transducer output signals and said calibration data.

2. The method of claim 1, including the step of determining whether the measured output signals of the mounted transducer constitute a usable blood pressure measurement.

3. The method of claim 1, wherein said step of collecting calibration data includes receiving the outputs of said accurate and diagnostically meaningful blood pressure measuring device, simultaneously measuring the output signals of the mounted transducer and storing the measured values from the measured output signals of the transducer and corresponding outputs from the diagnostically accurate blood pressure measuring device as a calibration table for use in said computing step.

4. The method of claim 3, wherein said calibration further includes determining whether said measured output signals of the mounted transducer are usable for blood pressure measurement, and using only usable data and corresponding outputs of the accurate and diagnostically meaningful blood pressure measuring device to form the calibration table.

5. A method of blood pressure monitoring, comprising the steps:

mounting a transducer on a user's body so that it detects at least one of spatial displacement and pressure variations caused by blood flow through an artery;

collecting calibration data for the transducer while so mounted by comparing a transducer output signal with an output from a blood pressure measuring device which provides accurate and diagnostically meaningful blood pressure results;

determining a base pressure applied to the transducer by the mounting step to maintain substantially constant pressure on the transducer within a predetermined range of values;

measuring the output signals of said mounted transducers;

computing blood pressure from at least said measured transducer output signals and said calibration data; and evaluating a computed blood pressure to determine if it falls within a predetermined range, and storing at least values outside of said range.

6. The method of claim 1, including the further step of evaluating a computed blood pressure to determine if it falls within a predetermined range, and activating an alarm detectable by the user when the computed blood pressure falls outside of said range.

7. The method of claim 1, wherein, and the steps of mounting the transducer on a user's body, collecting calibration data, determining the pressure applied to the transducer, measuring output signals of said mounted transducer and computing blood pressure are perfomed by a portable unit separate from but adapted to be operably connected to said diagnostically accurate blood pressure measuring device during said collecting calibration data step and disconnected thereafter.

8. The method of claim 7, wherein the portable unit is operably coupled to the diagnostically accurate blood pressure measuring device during the calibration step by a wireless transmission.

9. The method of claim 7, wherein the portable unit is operably coupled to the diagnostically accurate blood pressure measuring device during the calibration step by a removable cable connection.

10. The method of claim 7, and including forming the diagnostically accurate blood pressure measuring device as a cuff sphygmomanometer.

11. The method of claim 7, wherein the portable unit is shaped and sized to be mounted on the user on a continuous basis during the measuring and computing steps without interfering with the user's normal activities.

12. The method of claim 11, and including forming said portable unit in the shape of a wristwatch suitable for mounting on the wrist of a user.

13. The method of claim 1, and including forming the transducer to provide output signals representative of the movement of an arterial wall in response to the pumping of blood by the heart.

14. The method of claim 1, including the further step of automatically maintaining the base pressure on the transducer within a predetermined range of values in response to the determined values of the pressure applied to the transducer by the mounting step.

15. The method of claim 1, including the further step of manually monitoring the base pressure on the transducer within a predetermined range of values in response to the determined value of the base pressure applied to the transducer by the mounting step.

16. The method of claim 1, and including forming the transducer to provide an output signal representative of the base pressure applied thereto by the mounting step for use in the determining step.

17. The method of claim 1, and including computing said blood pressure from at least the measured transducer output, said calibration data and data interpretation criteria.

18. The blood pressure monitoring method of claim 1, including the step of selecting a blood pressure measuring device which is accepted by the medical community as providing accurate and diagnostically meaningful blood pressure results.

19. A method of blood pressure monitoring, comprising the steps of:
mounting a transducer on a user's body so that it detects at least one of spatial displacement and pressure variations caused by blood flow through an artery;
operatively couple an accurate and diagnostically meaningful blood pressure measuring device which provides accurate and diagnostically meaningful blood pressure results to a user's body and operatively coupling the transducer and diagnostically meaningful blood pressure measuring device;
collecting calibration data for the transducer while so mounted by comparing a transducer output signal with an output from said diagnostically meaningful blood pressure measuring device to provide a stored calibration table having a plurality of values;
operatively separating the transducer and diagnostically meaningful blood pressure measuring device and physically disconnecting the diagnostically meaningful blood pressure measuring device from the user's body, so that the collection of calibration data is discontinued;
after separating and disconnecting the blood pressure measuring device, measuring the output signals of the mounted transducer; and
computing blood pressure from at least the transducer output signals and said calibration data from said calibration table.

20. The method of claim 19, including the step of determining whether the measured output signals of said mounted transducer constitute a usable blood pressure measurement.

21. The method of claim 19, wherein said step of collecting calibration data includes receiving the outputs of said diagnostically accurate blood pressure measuring device, simultaneously measuring output signals of said mounted transducer and storing the measured values from the measured output signals of the transducer and corresponding outputs from the diagnostically accurate blood pressure measuring device as a calibration table for use in said computing step.

22. The method of claim 21, wherein said calibration further includes determining whether said measured output signals of said mounted transducer are usable for blood pressure measurement, and using only usable data and corresponding outputs of the diagnostically accurate blood pressure measuring device to form the calibration table.

23. The method of claim 19, including the further step of evaluating a computed blood pressure to determine if it falls within a predetermined range, and storing at least values outside of said range.

24. The method of claim 19, including the further step of evaluating a computed blood pressure to determine if it falls within a predetermined range, and activating an alarm detectable by the user when the computed blood pressure falls outside of said range.

25. The method of claim 19, wherein and the steps of mounting the transducer on a user's body, collecting calibration data, determining the pressure applied to the transducer, measuring outputs of said mounted transducer and computing blood pressure are performed by a portable unit separate from but adapted to be operably connected to said diagnostically accurate blood pressure measuring device during said collecting calibration data step and disconnected thereafter.

26. The method of claim 25, and including shaping and sizing the portable unit so that it may be mounted on the user on a continuous basis during the measuring and computing steps without interfering with the user's normal activities.

27. The method of claim 26, and including forming the portable unit in the shape of a wristwatch suitable for mounting on the wrist of a user.

28. The method of claim 25, and including operably coupling the portable unit to the accurate and diagnostically meaningful blood pressure measuring device during the calibration step by a wireless transmission.

29. The method of claim 25, and including operably coupling the portable unit to the accurate and diagnostically meaningful blood pressure measuring device during the calibration step by a removable cable connection.

30. The method of claim 25, and including forming the accurate and diagnostically meaningful blood pressure measuring device as a cuff sphygmomanometer.

31. The method of claim 19, and including forming the transducer to provide output signals representative of the movement of an arterial wall in response to the pumping of blood by the heart.

32. The method of claim 19, and including forming the transducer to provide an output representative of the base pressure applied thereto by the mounting step for use in the determining step.

33. The method of claim 19, and including the further step of determining the base pressure applied to the transducer by the mounting step and determining if that pressure is within a predetermined range of values.

34. The method of claim 33, and including the further step of manually adjusting the mounting of the transducer to set the base pressure applied to the transducer to a value within said predetermined range of values.

35. The method of claim 33, and including the further step of automatically adjusting the mounting of the transducer to bring the base pressure to within said predetermined range of values in response to the determined pressure.

36. The method of claim 33, wherein said step of determining the base pressure on the transducer is performed before collecting calibrating data and before measuring the output signals of the mounted transducer for use in computing blood pressure.

37. The method of claim 19, and including computing said blood pressure from at least measured transducer output, said calibration data and data interpretation criteria.

38. The blood pressure monitoring method of claim 19, including the step of selecting a blood pressure measuring device which is accepted by the medical community as providing accurate and diagnostically meaningful blood pressure results.

39. A blood pressure monitoring device for monitoring arterial blood pressure from an artery of a user by use of a separate diagnostically accurate blood pressure measuring device for calibration, comprising:

a transducer producing an output in response to at least one of spatial displacement and pressure variations caused by blood flow through an artery;

means for mounting said transducer on a user's body so that the transducer can detect at least one of spatial displacement and pressure variations caused by blood flow through an artery;

means for determining the base pressure applied to the transducer by the mounting means;

means for setting said base pressure to a level within a predetermined range of values;

means for measuring signal outputs of said mounted transducer;

means for selectively providing data representative of the blood pressure of a user as measured by a diagnostically accurate blood pressure measuring device;

means for collecting said diagnostically accurate blood pressure measuring device data and measured output signals of said mounted transducer representing essentially simultaneous measurements of blood pressure and storing these collected corresponding values; and means for computing blood pressure from at least said measured output signals of said mounted transducer and said collected corresponding values with said means for computing blood pressure and said means for collecting disconnected from said diagnostically accurate blood pressure device.

40. The blood pressure monitoring device of claim 39, wherein said blood pressure monitoring device includes a member shaped and sized to be mounted on the body of the user as a unit without interference with the normal activities of the user, said member carrying said transducer mounting means, determining means, setting means, measuring means, collecting means and computing means but being separate from said blood pressure measuring device.

41. The blood pressure monitoring device of claim 40, wherein said member is in the form of a wristwatch, said means for mounting said transducer on a user's body comprising strap means for circling the limb of a user, and including a case supporting the components of the monitoring device carried by said member but not supported by said strap means, separate and apart from said diagnostically accurate blood pressure measuring device.

42. The blood pressure monitoring device of claim 41, wherein said transducer is mounted on said strap means.

43. The blood pressure monitoring device of claim 41, wherein said transducer is mounted within said strap means.

44. The blood pressure monitoring device of claim 41, wherein said means for setting the pressure applied to said transducer includes means for setting the effective length of said strap means adapted to extend about the limb of the user.

45. The blood pressure monitoring device of claim 44 including means supported on said case means for selectively adjusting the effective length of said strap means.

46. The blood pressure monitoring device of claim 44, wherein said strap means comprises two strap portions each having a first and second end, said two strap portions being respectively coupled on opposed sides of said case at its respective first end thereof and joinable at the respective second ends thereof, said means for adjusting the effective length of said strap means comprising means for adjusting the relative positions of the joinable second ends of said strap portions.

47. The blood pressure monitoring device of claim 41, wherein said means for selectively providing diagnostically accurate blood pressure measuring device data includes a receiver means in said unit for receiving such data by wireless transmission.

48. The blood pressure monitoring device of claim 41, wherein the means for selectively providing said diagnostically accurate blood pressure measuring device data includes cable input coupling means in said unit to which can be applied a cable carrying said diagnostically accurate blood pressure measuring device data.

49. The blood pressure monitoring device of claim 41, and including timekeeping means carried by said case and display means carried by said case for displaying time and blood pressure information.

50. The blood pressure monitoring device of claim 40, and including in said unit display means for displaying at least values of pressure applied to the transducer and computed blood pressure values.

51. The blood pressure monitoring device of claim 39, including means for determining whether the measured output signals of the mounted transducer constitute a usable blood pressure measurement.

52. The blood pressure monitoring device of claim 39, and including means for evaluating a computed blood pressure measurement to determine if it falls within a predetermined range and means for storing at least values outside said range.

53. The blood pressure monitoring device of claim 39, including alarm means, and means for evaluating a computed blood pressure to determine if it falls outside a predetermined range, and for activating said alarm means when the computed blood pressure falls outside said ranges.

54. The blood pressure monitoring device of claim 39, wherein said transducer is adapted to produce output signals representative of the movement of an arterial wall in response to the pumping of blood by the heart.

55. The blood pressure monitoring device of claim 39, wherein said diagnostically accurate blood pressure measuring device is a separate cuff sphygmomanometer.

56. The blood pressure monitoring device of claim 39, wherein said means for determining the pressure applied to the transducer by the mounting means is adapted to operate based on a measured value from said transducer.

57. The blood pressure monitoring device of claim 39, wherein said transducer is a piezoelectric transducer.

58. The blood pressure monitoring device of claim 39, wherein said transducer includes strain gauge means.

59. The blood pressure monitoring device of claim 39, wherein said transducer includes an aneroid chamber.

60. The blood pressure monitoring device of claim 39, wherein said transducer includes an optical motion sensor.

61. The blood pressure monitoring device of claim 39, wherein said computing means additionally uses data interpretation criteria.

62. A blood pressure monitoring device for monitoring arterial blood pressure from an artery of a user by use of a separate diagnostically accurate blood pressure measuring device for producing data representative of the blood pressure of the user when selectively operatively coupled to the user for calibration purposes, comprising:

a transducer for producing an output in response to variations caused by blood flow through an artery;

means for mounting said transducer on a user's body so that said transducer can detect at least one of spatial displacement and pressure variations caused by blood flow through an artery;

means for measuring output signals of said mounted transducer;

means for collecting data from said diagnostically accurate blood pressure measuring device and measured output signals of said mounted transducer representing essentially simultaneous measurements of blood pressure by said mounted transducer and said diagnostically accurate blood pressure measuring device when operatively coupled to the user and storing a plurality of these collected corresponding values, said collecting means being operatively coupled to said mounted transducer;

means for selectively connecting said diagnostically accurate blood pressure measuring device to said means for collecting data when said diagnostically accurate blood pressure measuring device is operatively and physically coupled to the user's body and for physically disconnecting said diagnostically accurate blood pressure measuring device from said means for collecting data when said diagnostically accurate blood pressure measuring device is not operatively and physically coupled with the user's body; and means operatively coupled to said transducer and to said means for collecting data for automatically computing blood pressure from said measured output signals of said mounted transducer and said collected corresponding values when said means for collecting data is disconnected from said diagnostically accurate blood pressure device, said computing means functioning even when said diagnostically accurate blood pressure measuring device is operatively and physically disconnected from the user.

63. The blood pressure monitoring device of claim 62, wherein said blood pressure monitoring device includes a member shaped and sized to be mounted on the body of the user as a unit without interference with the normal activities of the user, said member carrying said transducer, mounting means, measuring means, collecting means and said computing means but not said blood pressure measuring device.

64. The blood pressure monitoring device of claim 63, wherein said member is in the form of a wrist watch, said means for mounting said transducer on a user's body comprising strap means for circling the limb of a user, and including a case for supporting the components of said monitoring device carried by said member and not supported by said strap means, separate and apart from said diagnostically accurate blood pressure measuring device.

65. The blood pressure monitoring device of claim 64, wherein said tranducer is mounted on said strap means.

66. The blood pressure monitoring device of claim 64, and including timekeeping means carried by said case and display means for displaying at least time and blood pressure information.

67. The blood pressure monitoring device of claim 64 and including means for determining the pressure applied to the transducer by the mounting means and means for setting said pressure to a level within a predetermined range of values.

68. The blood pressure monitoring device of claim 67, wherein said means for setting said pressure to a level within a predetermined range of values comprises a manual adjustment of the mounting means.

69. The blood pressure monitoring device of claim 68, wherein said means for setting said pressure to a level within a predetermined range of values comprises an automatic adjustment of the mounting means.

70. The blood pressure monitoring device of claim 69 including means supported on said case means for selectively adjusting the effective length of said strap means.

71. The blood pressure monitoring device of claim 67, wherein said means for setting the pressure applied to said transducer includes means for setting the effective length of said strap means extending about the limb of the user.

72. The blood pressure monitoring device of claim 71, wherein said means for determining the pressure applied to the transducer by the mounting means is adapted to operate on a measured value from said transducer means.

73. The blood pressure monitoring device of claim 67, wherein in said strap means comprises two strap portions each having a first and second end, said two strap portions being respectively coupled on opposed sides of said case at its respective first end thereof and joinable at the respective second ends thereof, said means for adjusting the effective length of said strap means comprising means for adjusting the relative positions of the joinable second ends of said strap portions.

74. The blood pressure monitoring device of claim 64, wherein said transducer is mounted within said strap means.

75. The blood pressure monitoring device of claim 63, and including display means for displaying at least computed blood pressure values carried by said member.

76. The blood pressure monitoring device of claim 63, wherein said means for selectively connecting said diagnostically accurate blood pressure measuring device to said means for collection data includes a receiver means in said unit for receiving such data by wireless transmission.

77. The blood pressure monitoring device of claim 62, including means for determining whether the measured output signals of the mounted transducer constitute a usable blood pressure measurement.

78. The blood pressure monitoring device of claim 62, and including means for evaluating the computed blood pressure measurement to determine if it falls within one or more predetermined ranges and means for storing at least values outside said ranges.

79. The blood pressure monitoring device of claim 62, including alarm means, and means for evaluating said computed blood pressure to determine if it falls outside one or more predetermined ranges, and for activating said alarm means when the computed blood pressure falls outside said ranges.

80. The blood pressure monitoring device of claim 62, wherein the means for selectively providing said diagnostically accurate blood pressure measuring device data includes cable input coupling means in said unit to which can be applied a cable carrying said diagnostically accurate blood pressure measuring device data.

81. The blood pressure monitoring device of claim 62, wherein said transducer is adapted to produce output signals representative of the movement of an arterial wall in response to the pumping of blood by the heart.

82. The blood pressure monitoring device of claim 62, wherein said transducer is a piezoelectric transducer.

83. The blood pressure monitoring device of claim 62, wherein said diagnostically accurate blood pressure measuring device is a separate cuff sphygmomanometer.

84. The blood pressure monitoring device of claim 62, wherein said transducer includes strain gauge means.

85. The blood pressure monitoring device of claim 62, wherein said transducer includes an aneroid chamber.

86. The blood pressure monitoring device as claimed in claim 62, wherein said transducer includes an optical motion sensor.

87. The blood pressure monitoring device of claim 62, wherein said computing means additionally uses data interpretation criteria.

\* \* \* \* \*